(12) United States Patent
Miyagawa et al.

(10) Patent No.: US 6,734,295 B1
(45) Date of Patent: May 11, 2004

(54) MODIFIED CRE RECOMBINASE GENE FOR MAMMALS

(75) Inventors: Shuji Miyagawa, Ashiya (JP); Masaru Okabe, Minoo (JP)

(73) Assignee: President of Osaka University, Suita (JP)

( * ) Notice: Subject to any disclaimer, the term of this patent is extended or adjusted under 35 U.S.C. 154(b) by 64 days.

(21) Appl. No.: 09/662,128

(22) Filed: Sep. 14, 2000

(30) Foreign Application Priority Data

Sep. 17, 1999 (JP) ............................................ 11-264364

(51) Int. Cl.$^7$ ............................. C07H 21/02; C12N 5/00

(52) U.S. Cl. ....................................... 536/23.1; 435/325

(58) Field of Search ............................. 435/320.1, 325; 536/23.1; 800/21

(56) References Cited

FOREIGN PATENT DOCUMENTS

WO    WO 99/10488    3/1999

OTHER PUBLICATIONS

Rowe, PM (1996) Xenotransplantation: from animal facility to the clinic? Molecular Medicine Today, pp. 10–11 (Jan. 1996).*
Bradley et al. Modifying the Mouse: Design and Desire. May 1992. Biotechnology. vol. 10, pp. 534–539.*
Mullins and Mullins. Perspective Series: Molecular Medicine in Genetically Engineered Animals, Apr. 1, 1996, Clinical Investigation. vol. 97, No. 7, pp. 1557–1560.*
Campbell and Wilmut. Totipotency or Multipotentiality of Cultured Cells: Applications and Progress. Theriogenology. Jan. 1, 1997. vol. 47, No. 1, pp. 63–70.*
Nakamura et al., Codon usage tabulated from the international DNA sequence databases, 1998, Nucleic Acids Research, vol. 26, p. 334.*
Bergemann et al., Excision of specific DNA–sequences from integrated retroviral vectors via site–specific recombination, 1995, Nucleic Acids Research, vol. 23, pp. 4451–4456.*
St–Onge et al., Temporal control of the cre recombinase in transgenic mice by a tetracycline responsive promoter, 1996, Nucleic Acids Research, vol. 24, pp. 3875–3877.*
Zhang et al., An enhanced green fluorescent protein allows sensitive detection of gene transfer in mammalian cells, 1996, Biochemical and Biophysical Research Communicaations. vol. 227, pp. 707–711.*
Wall, Transgenic livestock: Progress and prospects for the future,. 1996, Theriogenology, vol. 45, pp. 57–68.*
Sigmund, Viewpoint: Are studies in genetically altered mice out of control?, 2000. Arterioscler Thromb Vasc Biol., vol. 20, pp. 1425–1429.*

"Lens–Specific Expression and Developmental Regulation of the Bacterial Chloramphenicol Acetyltransferase Gene Driven by the Murine αA–Crystallin Promoter in Transgenic Mice", Paul A. Overbeek, et al., Proc. Natl. Acad. Sci. USA, vol. 82, pp. 7815–7819, Dec. 1985.
"Targeted Oncogene Activation by Site–Specific Recombination in Transgenic Mice", M. Lakso, et al., Proc. Natl. Acad. Sci. USA, vol. 89, pp. 6232–6236, Jul. 1992.
"Site–Specific Recombination of a Transgene in Fertilized Eggs by Transient Expression of Cre Recombinase", Kimi Araki, et al., Proc. Natl. Acad. Sci. USA, vol. 92, pp. 160–164, Jan. 1995.
"Uniform Vascular–Endothelial–Cell–Specific Gene Expression in Both Embryonic and Adult Transgenic Mice", Thorsten M. Schlaeger, et al., Proc. Natl. Acad. Sci. USA, vol. 94, pp. 3058–3063, Apr. 1997.
"Tissue–Specific Knockout of the Mouse Pig–a Gene Reveals Important Roles for GPI–anchored Proteins in Skin Development", Masahito Tarutani, et al., Proc. Natl. Acad. Sci. USA, vol. 94, pp. 7400–7405, Jul. 1997.
"Tissue– and Site–Specific DNA Recombination in Transgenic Mice", Paul C. Orban, et al., Natl. Acad. Sci. USA, vol. 89, pp. 6861–6865, Aug. 1992.
"Microinjection of Cre Recombinase RNA Induces Site–Specific Recombination of a Transgene in Mouse Oocytes", Ton de Wit, et al., Nucleic Acids Research, vol. 26, No. 2, pp. 676–678, 1998.
"Condon Usage Tabulated from the International DNA Sequence Databases", Yasukazu Nakamura, et al., Nucleic Acids Research, vol. 26, No. 1, p. 334, 1998.
"Genomic Targeting with Purified Cre Recombinase", Wendy Baubonis, et al., Nucleic Acids Research, vol. 21, No. 9, pp. 2025–2029, 1993.
"Targeted Integration of DNA Using Mutant Lox Sites in Embryonic Stem Cells", Kimi Araki, et al., Nucleic Acids Research, vol. 25, No. 4, pp. 868–872, 1997.
"Efficient Production of Cre–Mediated Site–Directed Recombinants Through the Utilization of the Puromycin Resistance Gene, PAC: a Transient Gene–Integration Marker for ES Cells", Masahiko Taniguchi, et al., Nucleic Acids Research, vol. 26, No. 2, pp. 679–680, 1998.
"Codon Usage Patterns in *Escherichia coli, Bacillus Subtilis, Saccharomyces Cerevisiae, Schizosaccharomyces Pombe, Drosophila Melanogaster* and *Homo Sapiens*: A Review of the Considerable within–Species Diversity", Paul M. Sharp, et al., Nucleic Acids Research, vol. 16, No. 17, pp. 8207–8211, 1988.

(List continued on next page.)

*Primary Examiner*—Anne-Marie Falk
*Assistant Examiner*—Celine Qian
(74) *Attorney, Agent, or Firm*—Oblon, Spivak, McClelland, Maier & Neustadt, P.C.

(57) ABSTRACT

An object of the present invention is to provide a modified gene for mammals having expression level, in mammalian cells, tissues, organs or bodies, several times as high as that of phage-derived Cre recombinase. To attain the aforementioned object, the present invention provides a modified Cre recombinase gene for mammals consisting of codons frequently used in mammalian cells.

5 Claims, 5 Drawing Sheets

OTHER PUBLICATIONS

"Condon Usage Tabulated from the GenBank Genetic Sequence Data", Ken–Nosuke Wada, et al., Nucleic Acids Research, vol. 18, Supplement, 1990.

"Multiple Tissue–Specific Elements Control the Apolipoprotein E/C–1 Gene Locus in Transgenic Mice", W. Scott Simonet, et al., The Journal of Biological Chemistry, vol. 266, No. 14, pp. 8651–8654, May 1991.

"Transgenic Analysis of the Thyroid–Responsive Elements in the α–Cardiac Myosin Heavy Chain Gene Promoter", Arun Subramaniam, et al., The Journal of Biological Chemistry, vol. 268, No. 6, pp. 4331–4336, Feb. 1993.

"A Far–Downstream Hepatocyte–specific Control Region Directs Expression of the Linked Human Apolipoprotein E and C–I Genes in Transgenic Mice", W. Scotto Simonet, et al., The Journal of Biological Chemistry, vol. 268, No. 11, Apr. 1993.

"Independent Control of Immunoglobulin Switch Recombination at Individual Switch Regions Evidenced through Cre–loxP–Mediated Gene Targeting", Hua Gu, et al., Cell, vol. 73, pp. 1155–1164, Jun. 1993.

"Enhanced Expression in Tobacco of the Gene Encoding Green Fluorescent Protein by Modification of its Codon Usage" Gerard J.A. Rouwendal, et al., Plant Molecular Biology, 33, pp. 989–999, 1997.

"Overexpression of Low Density Lipoprotein (LDL) Receptor Eliminates LDL from Plasma in Transgenic Mice", Sandra L. Hofmann, et al., Science, vol. 239, pp. 1277–1281, Mar. 1988.

"Deletion of a DNA Polymerase β Gene Segment in T Cells Using Cell Type–Shock Gene Targeting", Hua Gu, et al., Science, vol. 265, pp. 103–106, Jul. 1994.

"Codon Usage Limitation in the Expression of HIV–1 Envelope Glycoprotein" J. Haas, et al., Current Biology, vol. 6, No. 3, pp. 315–324, 1996.

"Recycling Selectable Markers in Mouse Embryonic Stem Cells", A Abuin, et al., Molecular and Cellular Biology, vol. 16, No. 4, 1851–1856, Apr. 1996.

"Heart–Specific Targeting of Firefly Luciferase by the Myosin Light Chain–2 Promoter and Developmental Regulation in Transgenic Mice", Wolfgang–Michael Franz, et al., Circulation Research, vol. 73, No. 4, pp. 629–638, Oct. 1993.

"Yeast–Enhanced Green Fluorescent Protein (yEGFP): A Reporter of Gene Expression in Candida Albicans", Brendan P. Cormack, et al., Microbiology, 143, pp. 303–311, 1997.

"Bacteriophage P1 cre Gene and its Regulatory Region Evidence for Multiple Promoters and for Regulation by DNA Methylation", N. Sternberg, et al., Journal of Molecular Biology, vol. 187, No. 2, pp. 197–212, Jan. 1986.

"Structure of Cre Recombinase Complexed with DNA in a Site–Specific Recombination Synapse", Feng Guo, et al., Nature, vol. 389, Sep. 1997, pp. 40–46.

"Efficiency of Recombination by Cre Transient Expression in Embryonic Stem Cells: Comparison of Various Promoters", K. Arai, et al., J. Biochem, 122, pp. 977–982, 1998.

"Translation is Enhanced after Silent Nucleotide Substitutions in A+T–Rich Sequences of the Coding Region of CD45 cDNA", J. Milland, et al., Eur. J. Biochem, 238, pp. 221–230, 1996.

"Synthesis of a New Cre Recombinase Gene Based on Optimal Codon Usage for Mammalian Systems", Y. Koresawa, et al., J. Biochem, vol. 127, No. 3, pp. 367–372, 2000.

Antonella Forlino, et al., The Journal of Biological Chemistry, vol. 274, No. 53, pp. 37923–37931, "Use of the Cre/lox Recombination System to Develop a Non–Lethal Knock–In Murine Model for Osteogenesis Imperfecta with an α 1(l) G349C Substitution", Dec. 31, 1999.

Brian Sauer, Methods: A Companion to Methods in Enzymology, vol. 14, No. 4, pp. 381–392, "Inducible Gene Targeting in Mice Using The Cre/lox System", 1998.

Brian Sauer, et al., Proc. Natl. Acad. Sci. USA, vol. 85, No. 14, pp. 5166–5170, "Site–Specific DNA Recombination in Mammalian Cells by the Cre Recombinase of Bacteriophage P1", Jul. 1988.

* cited by examiner

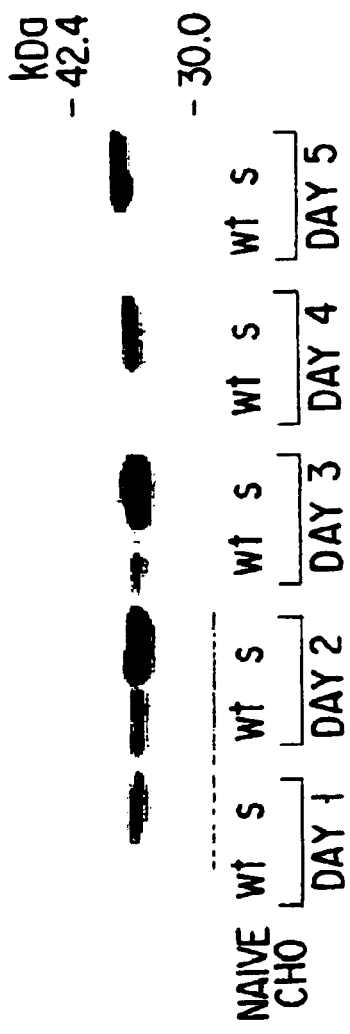
FIG. 4A-I cre
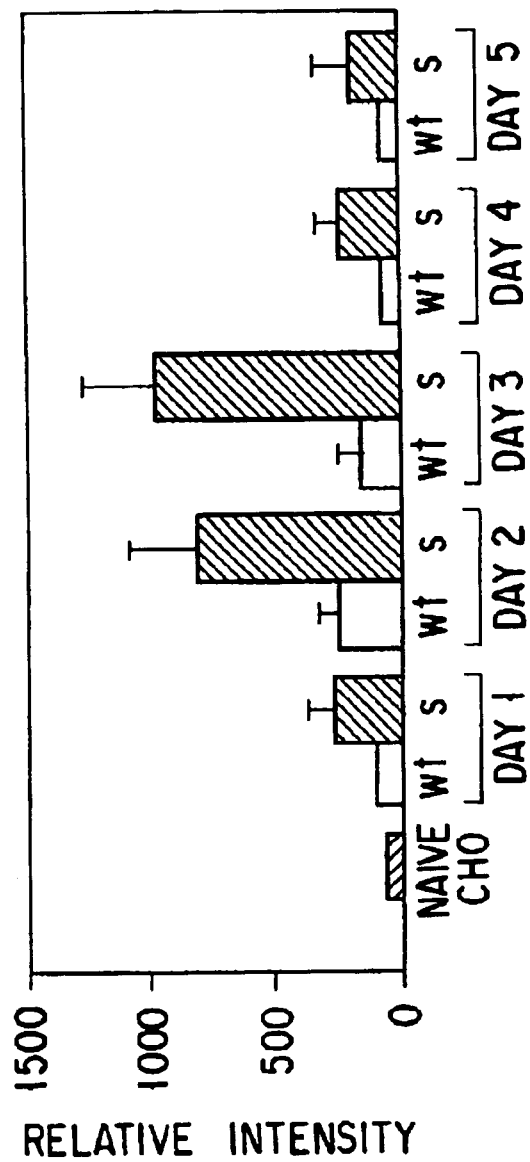
FIG. 4A-II

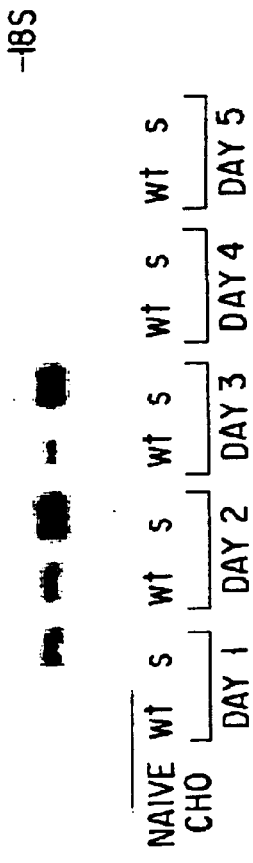
FIG. 4B-I
FIG. 4B-II
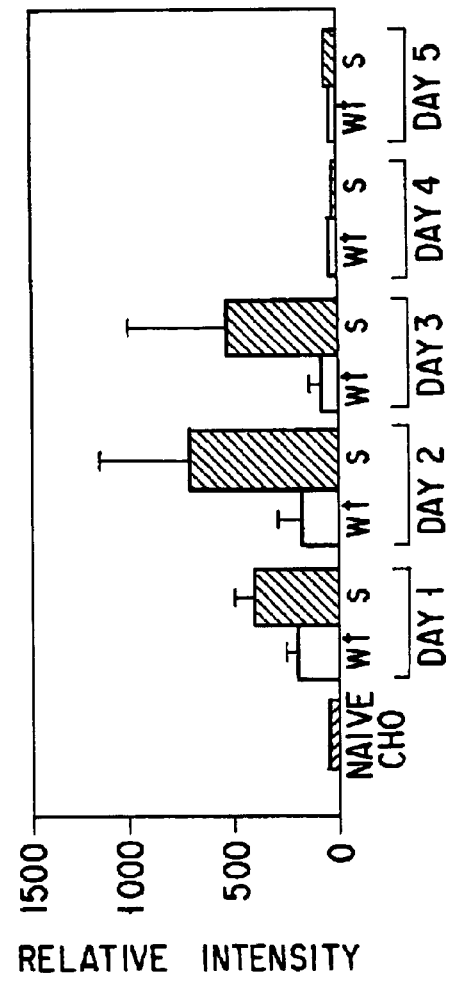
FIG. 4B-III

MODIFIED CRE RECOMBINASE GENE FOR MAMMALS

CROSS-REFERENCE TO RELATED APPLICATIONS

This application is based upon and claims the benefit of priority from the prior Japanese Patent Application No. 11-264364, filed Sep. 17, 1999, the entire contents of which are incorporated herein by reference.

BACKGROUND OF THE INVENTION

The site-specific recombination is a phenomenon found in the process in which λ phage DNA is integrated into a host chromosome. The site specific recombination is mediated by a recombination enzyme called recombinase which catalyzes recombination by recognizing a relatively short specific sequence, whereas the homologous recombination is performed by pairing long homologous nucleic acids. In this respect, the site specific recombination is a biological event completely different from the homologous recombination.

The site-specific recombination can be used to selectively recombinize a gene construct having a desired gene bound thereto, thereby knocking-in or knocking-out the desired gene. Therefore, the site-specific recombination is a very useful technique, especially in the field of embryological engineering for knocking-out or knocking-in a specific gene in a time- or location-controlled manner.

Now, referring to FIG. 1, the mechanism of the site-specific recombination and its application will be explained in brief.

As shown in FIG. 1, unlike the homologous recombination which is initiated with DNA pairing, the site-specific recombination is triggered with binding of recombinase 1 to a specific sequence 3 in DNA 2 to form a DNA-protein complex 5. The recombinase 1 bound to DNA 2 recognizes and binds to a specific sequence 4 which is present in the same DNA 2 or a different DNA and which has the same nucleotide sequence as the specific sequence 3. FIG. 1 shows the case where the specific sequence 3 and 4 are present in the same DNA. The recombinase bound to the specific sequence 3 and 4 catalyses a cleaving/rebinding reaction of single-strand DNA. More specifically, the reaction is performed by two steps: sequentially cleaving the 3' ends of the specific sequence 3 and 4; and binding a cleaved portion of the specific sequence 3 to a site A' and a cleaved portion of the specific sequence 4 to a site A.

As shown in FIG. 1, in the case where the specific sequences are present in the same DNA, the DNA is cleaved into two, one a straight DNA, and the other a cyclic DNA, by the site-specific recombination. The cyclic DNA falls out from the original DNA.

Therefore, if a gene construct having a desired gene arranged to be fallen off as the cyclic DNA, and a recombinase gene are introduced into a chromosome, and then, the recombinase gene is expressed in a time-controlled and/or location-controlled manner, only the corresponding gene is knocked-out in the time-controlled and/or location-controlled manner.

Alternatively, a gene construct and a recombinase can be introduced into a chromosome to selectively "knock-in" a desired gene in the gene construct. In the gene construct, the desired gene is placed downstream of a first specific sequence and a promoter is placed upstream of a second sequence such that the gene is transferred to be flanked with the promoter after a recombination process in which an intervening sequence between the promoter and the gene is fallen off. Accordingly, knock-in is achieved in time and location controlled manner by expression of the recombinase.

As the recombinase which catalyses the site-specific recombination, FRT recombinase and FLP recombinase which are derived from a yeast, and phage-derived Cre recombinase have been found. However, the yeast-derived FRT and FLP recombines do not work well in mammalian cells.

In contrast, the Cre-loxP system consisting of Cre recombinase and a loxP sequence, which is specifically recognized by Cre recombinase, can be applied to mammalian cells. Therefore, the Cre-loxP system is used to initiate the site-specific recombination in mammals.

However, since the Cre recombinase is a bacteriophage-derived protein, the codons in the Cre recombinase is not translated efficiently in mammalian cells. Therefore, the Cre recombinase has a drawback in that it is expressed insufficiently.

The present invention is made to overcome the aforementioned drawback associated with the phage-derived Cre recombinase gene. An object of the present invention is to provide a modified Cre recombinase gene for mammals that is expressed in mammalian cells, tissues, organs, or body several times as abundantly as the phage-derived Cre recombinase gene.

BRIEF SUMMARY OF THE INVENTION

To solve the aforementioned object, the present invention provides a modified Cre recombinase gene for mammal (SEQ ID NO:1).

The present invention is to provide a modified Cre recombinase gene for mammals having a nucleotide sequence represented by (SEQ ID NO:1).

The modified Cre recombinase gene for mammals of the present invention encodes the same Cre recombinase protein derived from a bacteriophage P1 having an amino acid sequence represented by (SEQ ID NO:2). However, all codons are modified into those most frequently used in swine DNA. Therefore, the modified Cre recombinase gene of the present invention is expressed more abundantly in mammals compared to the phage-derived Cre recombinase gene.

Furthermore, the present invention provides a method of knocking-in or knocking-out a desired gene by the modified Cre recombinase gene in a location-controlled and/or time-controlled manner.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 4A-I, 4A-II, 4B-I, 4B-II and 4B-III are Graphs and Western blottings showing the results of Example 2 in which transcription and translation rate of a CDNA of the gene of present invention and that of virus-derived Cre recombinase gene were compared in;

DETAILED DESCRIPTION OF THE INVENTION

Figure 1:
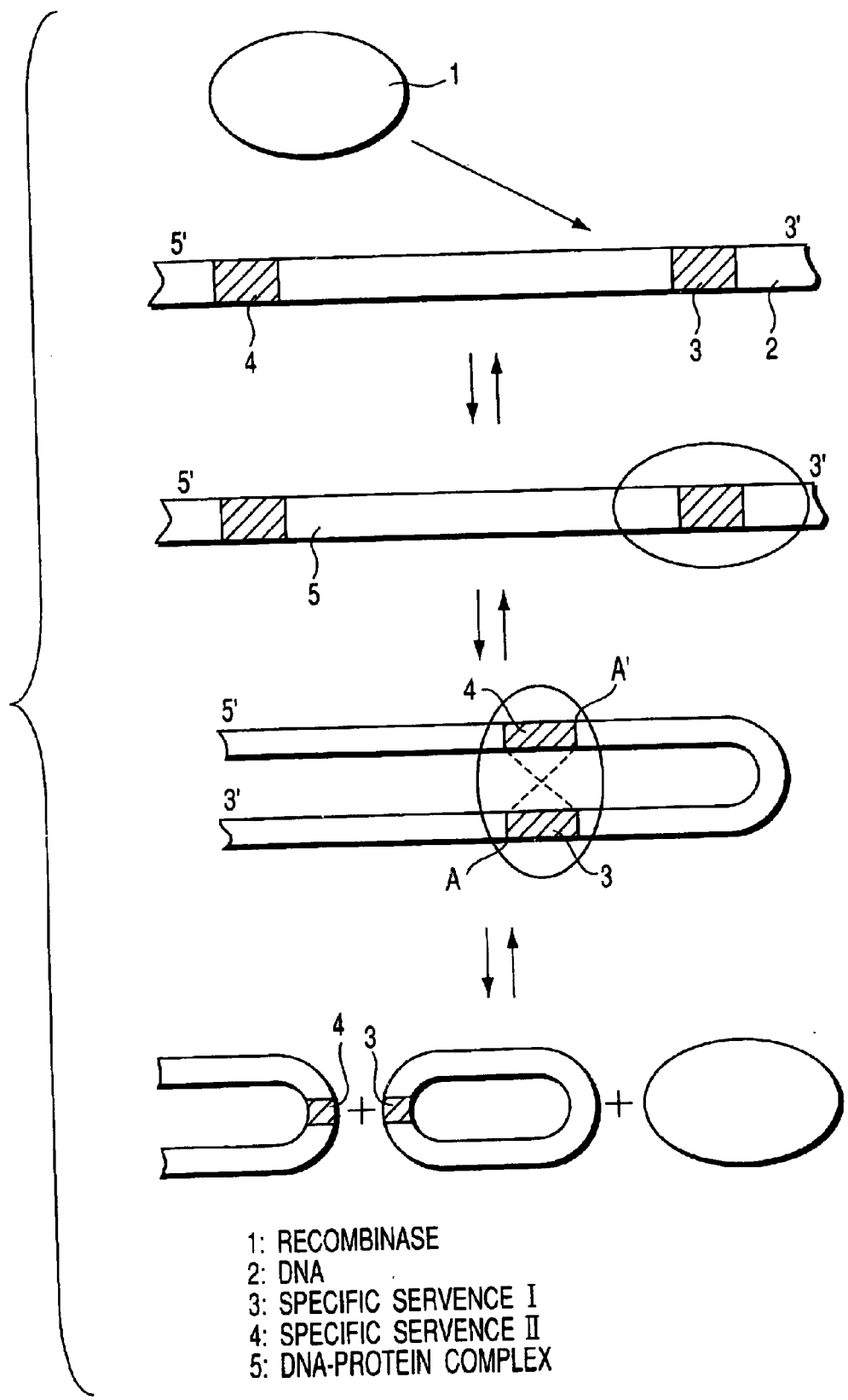
FIG. 1 is a schematic illustration of a mechanism of site-specific recombination.

More specifically, the codons used herein are as follows (the codons in parentheses are those most frequently used in bacteriophage P1).

Ala:GCC(GCT), Arg:CGC(CGC), Asn:AAC(AAT), Asp:GAC(GAT), Cys:TGC(TGT), Gln:CAG(CAG), Glu:GAG(GAA), Gly:GGC(GGT), His:CAC(CAT), Ile:ATC(ATT), Leu:CTG(CTG), Lys:AAG(AAA), Pro:CCC(CCT), Phe:TTC(TTT), Ser:AGC(TCA), Thr:ACC(ACA), Tyr:TAC(TAT), Val:GTG(GTT)

Note that Met and Trp are not modified since they are encoded only by a single codon.

The codons most frequently used in CDNA of mammals, other than humans such as swine and murines, are the same as the aforementioned codons except Arg. Therefore, the modified Cre recombinase gene for mammals of the present invention can be applied to other mammals. However, if there is a codon whose frequency differs from that of humans, it is preferable that the codon be modified. For example, the codon of Arg, namely, CGG, is preferably modified to CGC in swine and AGA in murines.

The frequency of each of the codons used in cDNA is known with respect to many mammals other than swine and murines. Therefore, the most suitable codon can be selected on the basis of the data of frequency.

No significant difference is observed in frequency in use of each of the codons among mammals. Therefore, the modified Cre recombinase gene for mammals of the present invention can be applied to any mammals even if the codon frequency in a given mammal is unknown. The most frequently used codon for Arg differs between humans, swine and murines. However, since six types of codons for Arg are used with substantially same frequency, even if the codon most frequently used is unknown, no significant problem is posed.

Accordingly, it should be noted that the present invention includes not only a polynucleotide represented by sequence number 1 but also a polynucleotide obtained by slightly modifying the aforementioned polynucleotide so as to apply it to various mammals other than humans.

Depending upon the expression level required, it is not necessary to replace all codons in a polynucleotide. However, it is generally preferable that all codons should be replaced.

As described, the "modified Cre recombinase gene for mammals" used herein refers to a Cre recombinase gene modified such that it is suitable for use in mammals. The gene is modified so as to having an elevated expression level in mammalian bodies and living tissues, compared to the phage-derived one. Accordingly, use of the gene of the present invention enables to improve efficiency of site-specific recombination in mammalian bodies, organs, tissues, and cells.

More specifically, the expression level of the modified Cre recombinase gene for mammals of the present invention is at least 2–3 times, generally, several times as high as that of the phage-derived one.

The present invention provides a polynucleotide having the modified Cre recombinase gene for mammals to which a regulatory sequence, a marker gene, a nucleotide transport signal, or a Kozak sequence is bound.

The "regulatory sequence" used herein refers to a nucleic acid sequence which is responsible for an increase/decrease of transcription rate. The regulatory sequence may be, but not limited to, a promoter, enhancer, upstream activation sequence, silencer, upstream suppressor sequence, and attenuator. Each of these regulatory sequences has to be operably linked to the modified Cre recombinase gene for mammals.

The regulatory sequence preferably linked to the modified Cre recombinase gene for mammals is a promoter. More particularly, an inducible promoter is preferred. There are many kinds of inducible promoters that induce gene expression upon interaction with such substances as nutritional elements, hormones, and substrates and the like or by stimulation such as temperature, electromagnetic wave, and oxidative stress and the like. Accordingly, it will be quite easy for one skilled in the art to select an appropriate promoter. Among inducible promoters are included a location-specific promoter and time-specific promoter.

When the inducible promoter is linked to the modified Cre recombinase gene for mammals, it is preferable that the promoter be induced by a substance location-specifically and time-specifically present at the location at which the modified Cre recombinase gene for mammals is to be expressed.

The "marker gene" is a gene indicating that the modified Cre recombinase gene for mammals is introduced into a target and expressed. The marker gene may be, but not limited to, a drug-resistant gene and a gene encoding a luminescent protein.

The "nucleic acid encoding a nuclear transport signal" refers to a nucleic acid encoding a nuclear transport signal (also called as a nuclear localizing signal) that functions as a signal for transporting a nuclear protein synthesized in a ribosome back into a nucleus. When the expressed Cre recombinase should be localized in the nuclear, the nucleic acid encoding the nuclear transport signal has to be bound to the modified Cre recombinase gene for mammals.

The "Kozak sequence" is a consensus sequence located immediately upstream of a translation initiation site ATG (position −6 to −1). The most frequently appearing sequences from −6 to +4 is GCCRCCATGR (R means G or A). If the Kozak sequence is conserved, it may be possible to increase a translation rate in mammals.

The present invention provides a polynucleotide having a complimentary sequence to the modified Cre recombinase gene for mammals and a polynucleotide to which a regulatory sequence, the marker gene and the like are linked.

Vectors for introducing each of the polynucleotides into individuals, organs, tissues, or cells fall within the scope of the present invention. The individuals, organs, tissues and cells having the polynucleotide introduced therein also fall within the scope of the present invention. To introduce the polynucleotide into the individuals, organs, tissues or cells, an electroporation, a lipid, and a microinjection (which are well known to one skilled in the art), but not limited to, may be employed.

The modified Cre recombinase gene for mammals can be introduced into any mammalian animals. The modified Cre recombinase gene for mammals may be introduced into, but not limited to, organs including liver, lung, kidney, heart, pancreas, and digestive tracts such as intestine. The modified Cre recombinase gene for mammals may be introduced into, but not limited to, tissues including brain tissue, skin, subcutaneous tissue, epithelium tissue, bone tissue, muscle tissue, and the like. The modified Cre recombinase gene for mammals may be introduced into, but not limited to, cells including all cells constituting the aforementioned organs and tissues, especially, liver cells, pancreatic cells as well as ovary cells, fertilized cells and embryonic stem cells.

The present invention provides a method for knocking-in a desired gene by use of a site-specific recombination reaction which is catalyzed by the Cre recombinase in a location-controlled manner and/or time-controlled manner.

In the method, a first gene construct comprising the modified Cre recombinase gene for mammals and an inducible promoter liked thereto is used to site-specifically recombine a second gene construct comprising two loxP sequences, a desired gene to be knocked-in, and a promoter As the inducible promoter to be linked in the first gene construct, an inducible promoter can be used that is capable of inducing the expression of the modified Cre recombinase gene for mammals specifically at the site and/or at the time for a desired gene to be knocked-in. With such an inducible promoter the second gene construct will be recombined specifically at a desired site and/or desired time.

Figure 2:
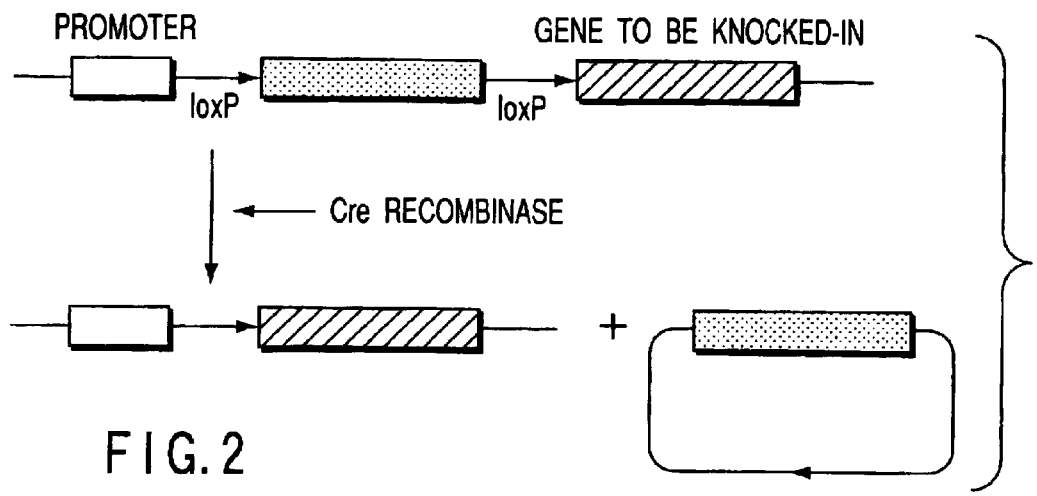
FIG. 2 is a schematic illustration of a method of knocking-in a desired gene in a time and/or location controlled manner by using a modified Cre recombinase gene for mammals of the present invention.

The promoter present in the second gene construct is arranged upstream of a first loxP sequence which is present upstream of the other loxP sequence, as shown in FIG. 2. The promoter must be arranged so as to induce the expression of the desired gene to be knocked-in, in other words, so as to render a desired gene functional.

Since the desired gene is placed downstream of the second loxP sequence, an interposed sequence between two loxP sequences is fallen off to make the desired gene linked directly to the first loxP sequence when site-specific recombination is triggered with the specific recognition of loxP sequence by the Cre recombinase.

A wild-type loxP sequence derived from a bacteriophage P1 has a nucleotide sequence ATAACTTCGTATAGCATA-CATTATACGAAGTTAT (SEQ ID NO:3). However, loxP66 sequence (TTCGTATAGCATAGATTATACGAAGTTAT) (SEQ ID NO:4) and loxP71 sequence (ATAACTTCGTATAGCATACATTATACGAA) (SEQ ID NO:5) can also be used, in which a deletion is made artificially. Accordingly, the "loxP sequence" used herein may include not only wild one but modified ones which preserve function equivalent to the wild one.

The promoter is linked directly or in close proximity to the first loxP sequence. Therefore, the desired gene which is linked to the first loxP sequence by the site-specific recombination, initiates to be expressed under operation of the promoter.

Therefore, if the first and the second gene constructs are introduced into a desired vital tissue (i.e., organ, tissue or cell taken out from an individual living body) or a desired individual body, the desired gene can be expressed in a location-controlled and/or time-controlled manner.

The first and second gene constructs may be introduced to any vital tissue or individual body.

However, it is preferable that they should be introduced into the aforementioned living tissues or mammals which have been enumerated as being suitable recipients for introducing the modified Cre recombinase gene for mammals.

Transgenic animals to which a desired gene is knocked-in, in a location-controlled and/or time-controlled manner fall within the scope of the present invention. The organs, tissues or cells taken out from the transgenic animals also fall within the scope of the present invention.

Furthermore, the present invention includes the method of knocking-out a desired gene by use of the site-specific recombination in a location-controlled and/or time-controlled manner.

The method of knocking-out a desired gene is attained by the site specific recombination in the same manner as in the method of knocking-in a desired gene. The knocking-out method is basically performed in the same manner as the knocking-in method except that positions of a promoter sequence and a desired gene differ in the second construct.

Figure 3:
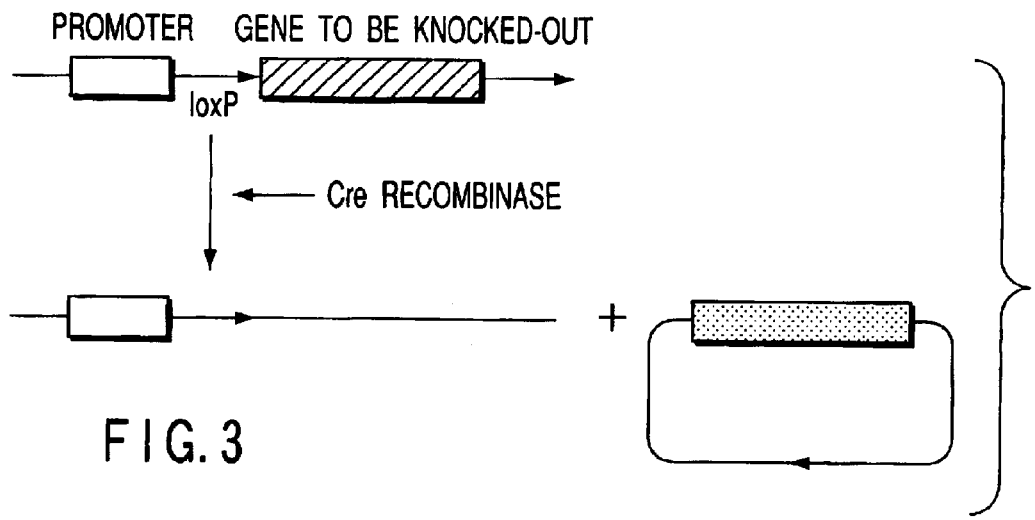
FIG. 3 is a schematic illustration of a method of knocking-out a desired gene in a time and/or location controlled manner by using the modified Cre recombinase gene for mammals of the present invention.

The knocking-out method and the typical structure of the second construct are schematically shown in FIG. 3.

The knocking-out method is primarily used to terminate the expression of a desired gene. Therefore, it is satisfactory if either the desired gene or the promoter sequence are knocked-out in its entirety or in part, or both of them are knocked-out from the second gene construct by the site-specific recombination. Therefore, possible arrangements for the loxP sequences, the promoter sequence, and the corresponding gene in the second construct are as follows:

①—promoter—loxP—corresponding gene—loxP—
②—loxP—promoter—corresponding gene—loxP—
③—loxP—promoter—loxP—corresponding gene—.

As a matter of fact, a single exon to a plurality of exons are generally knocked-out from the desired gene. Therefore, the term "desired gene" usually includes a whole or part of the desired gene.

Therefore, it should be noted that the step of "knocking-out a desired gene" in this text, includes directly knocking out the desired gene itself and knocking out a single to a plurality of exons or the promoter, thereby terminating its expression.

In this case, it is important to select a single to a plurality of exons which can terminate or decrease the activity of the protein to be knocked-out.

In the method of the present invention, the desired gene is generally present between two loxP sequences. Therefore, if the site specific recombination occurs in a location-controlled and/or time-controlled manner, the desired gene is knocked-out from the second gene construct. Hence, it is possible to terminate the expression of a specific gene in a location-controlled and/or time-controlled manner by the method of the present invention.

Any gene can be knocked-out by the method of the present invention. Therefore, the method of the present invention can be widely applied to various fields including the basic medical science and clinical medicine.

The transgenic animals from which a desired gene is knocked-out in a location-controlled and/or time-controlled manner in accordance with the method of the present invention fall within the scope of the present invention, organs, tissues or cells taken from the transgenic animals also fall within the scope of the present invention. Techniques for preparing the transgenic animals such as transgenic mouse and swine are well known to one skilled in the art.

It is possible to knock-in the first desired gene in a location-controlled and/or time-controlled manner and then knock-out the second desired gene in a location-controlled and/or time-controlled manner, in accordance with the aforementioned two methods. These methods, the transgenic animals created by these methods, organs, tissues, and cells taken from the transgenic animals fall within the scope of the present invention.

As an example, a transgenic swine can be produced for use in organ transplantation by knocking out a xenograft antigen from a specific organ in accordance with the method of the present invention. In the xenograft transplantation, a severe rejection occurs if the xenograft antigen is present. Therefore, if an animal from which the xenograft antigen is knocked-out, is used, the rejection can be avoided.

However, if the xenograft antigen is knocked-out from a whole body as in a conventional case, various diseases and disorders occur due to the absence of the xenograft antigen.

In contrast, in the method of the present invention, the transgenic swine is produced by knocking out the xenograft antigen from a specific organ, that is, only from a limited organ(s). Therefore, it is possible to prevent diseases or disorders caused by the absence of the antigen.

In the case of swine, it is preferable that a transgenic swine be formed by knocking out α 1,3 galactosyl transferase gene since aGal epitope is the biggest xenograft antigen.

Note that the term "xenograft antigen" refers to an antigenic substance present on a xenograft. The antigenic substance causes a rejection in the recipient which receives the xenograft.

The second example is cell transplantation attained by the method of the present invention. A gene construct is prepared by sandwiching a carcinogenic gene derived from a virus such as SV40 between two loxP sequences. Then this gene construct is introduced into the cell to be transplanted (transplant cell). The resultant cell becomes immortal, so that endless proliferation takes place. When the cells are proliferated to a predetermined level, the Cre recombinase is expressed to remove the carcinogenic gene thereby terminating the proliferation. The proliferation-terminated transplant cell is then transplanted to a recipient.

The transplant cell may be, but not limited to, a liver cell and pancreatic cell.

In a third example, an anti antibody-production-associated-molecule antibody can be knocked-out in a location-controlled and/or time-controlled manner by the method of the present invention.

The term "anti antibody-production-associated-molecule antibody" used herein refers to an antibody against the molecule which directly or indirectly participates in an antibody production mechanism. The anti antibody-production-associated-molecule antibody may be, but not limited to CD3, CD4, CD28, CTLA4, CD80, T cell receptor, major histocompatibility-compatible antigen, cytokines such as IL-4, IL-5, IL-6, cytokine receptor, and the like.

The anti antibody-production-associated-molecule antibody can suppress an immunoreaction associated with transplantation. Therefore, if a virus vector into which the gene of this antibody is integrated, is introduced into a recipient, the rejection can be drastically suppressed.

However, immuno-suppression is only required in the early stage after the transplantation. If the immune system is suppressed continuously, a significant immunodeficiency will occur. Therefore, if the immune system is suppressed only in the beginning of the transplantation by the method of the present invention, the success rate of organ transplantation can be remarkably increased.

In the foregoing, the method of the present invention has been described in detail with reference to examples, particularly, transplantation. However, these examples are used for only illustrating the present invention. The present invention is not limited by these examples in any sense. One skilled in the art will readily understand that the other examples, such as construction of disease-models (by knocking-in or knocking-out a specific gene in a location-controlled manner or time-controlled manner), gene therapy, the animals and tissues thus obtained are included in the scope of the present invention.

Now, the present invention will be explained more specifically with reference to examples.

EXAMPLE 1

In this example, a Cre recombinase cDNA construct was synthesized by attaching to a cDNA of a Cre recombinase gene for mammals the nucleic acid sequence (CCCAAGAAGAAGAGGAAGGTG) (SEQ ID NO:6) encoding a nuclear transport signal: ProLysLysLysArgLysVal. The cDNA used above contains the following codons: Ala:GCC, Arg:CGC, Asn:AAC, Asp:GAC, Cys:TGC, Gln:CAG, Glu:GAG, Gly:GGC, His:CAC, Ile:ATC, Leu:CTG, Lys:AAG, Pro:CCC, Phe:TTC, Ser:AGC, Thr:ACC, Tyr:TAC, Trp:TGG, and Val:GTG. The resultant cDNA construct is compared with a conventional Cre recombinase gene with respect to the level of mRNA and protein.

The cDNA construct was introduced into an expression vector pCAGGS and then transfected into a CHO cell by electroporation. Thereafter, temporary expression was checked and compared. The results are shown in FIGS. 4A-I, 4A-II, 4B-I, 4B-II and 4B-III.

In FIGS. 4A-I, 4B-I and 4B-II, Western blotting is shown in the upper panel and Northern blotting is shown in the lower panel.

As is apparent from the Western blotting, the conventional Cre (wt-Cre) reached a peak on a second day and no expression was observed on a fourth day. Whereas, in the mammalian Cre(s-Cre), the expression level increased until a third day and expression was observed on a fifth day. The amount of the mammalian Cre protein at the third day was about 7 times as large as the conventional case.

According to the Northern blotting, no expression was observed with respect to mRNA at the third day in both cases. However, mRNA of the mammalian Cre protein (in amount) on a second day and a third day reached 4.2 fold and 6.6 fold as large as the conventional case, respectively.

Note that GAPDH is an index of the amount of mRNA applied onto a gel.

EXAMPLE 2

Figure 5:
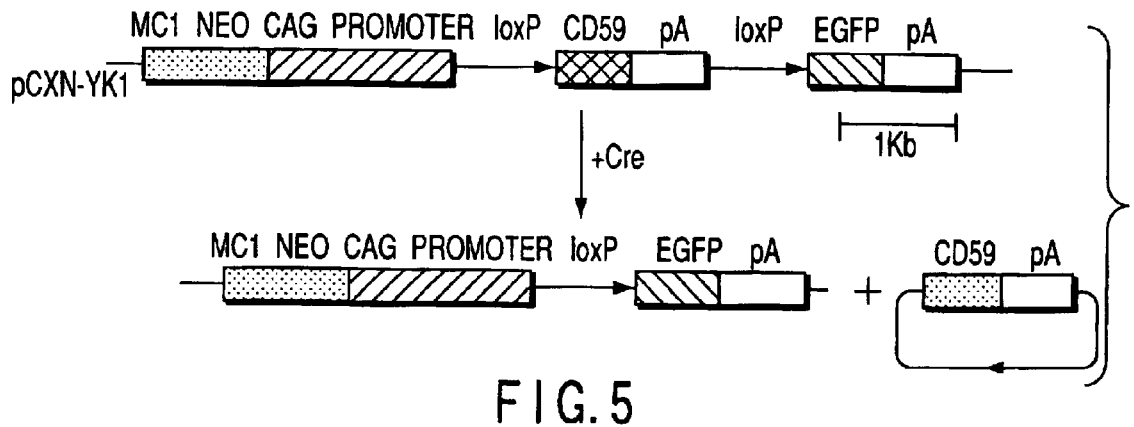
FIG. 5 is a schematic illustration of a gene construct used in Embodiment 2.

In this experiment, frequency of recombination in the presence of the cDNA of the modified Cre recombinase or that of conventional one is checked by use of a gene construct pCXN-YK1 (FIG. 5) containing two loxP sequences and a CAG promoter. The difference in frequency between the two cases was checked.

A gene construct pCXN-YK1 was constructed and transfected in a CHO cell to form a stable cell line (clone 29 and clone 30).

Figure 6:
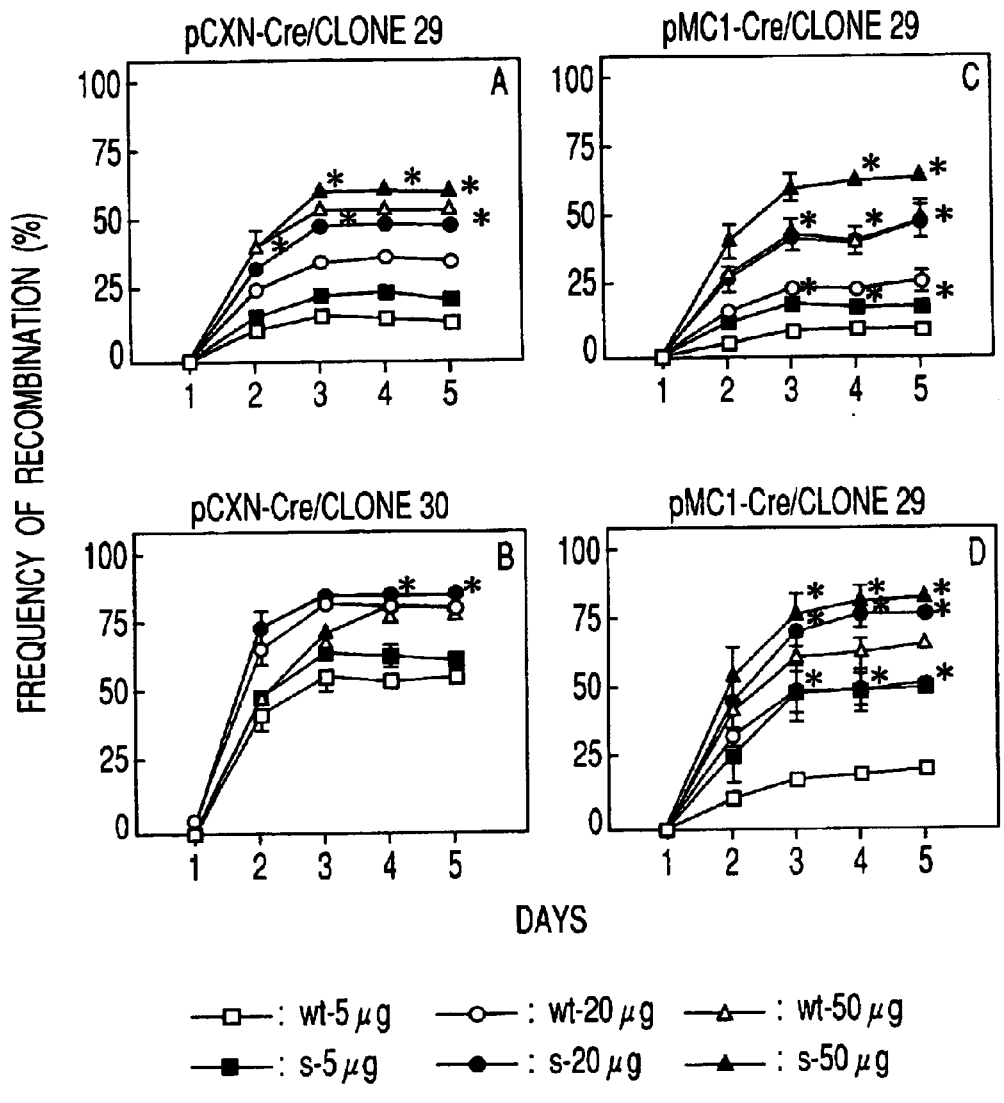
FIG. 6 is a Graphs showing difference in recombination frequency in a mammalian Cre-loxP and a conventional Cre-loxP.

Now, the conventional Cre CDNA and modified Cre cDNA (the amounts are shown in FIG. 6) were introduced respectively in expression vectors PCXN and pMC1. pCXN has a strong promoter activity while pMC1 has a relatively weak promoter activity. The two cDNAs were transfected into clone 29 and clone 30, respectively by electroporation. Thereafter, a frequency of recombination caused by Cre-loxP was evaluated. The expression vector pCXN includes a CAG promoter and an enhancer of cytomegalovirus. The expression vector pMC1 includes a thymidinekinase promoter and an enhancer of polyoma virus.

As is shown in FIG. 6 (see pMC1-Cre/clone 29 (Panel C) and pMC1-Cre/clone 30 (Panel D)), the modified Cre cDNA shows significantly higher recombination frequency (T study) compared to the conventional one with respect to DNA amounts of 5, 20, and 50 µg.

In the case of pCXN-Cre/clone 29 (panel A, DNA amounts of 5 and 20 µg,), and in the case of pCXN-Cre/clone 30 (Panel B, DNA amount of 20 µg), the modified Cre cDNA shows a significantly high recombination frequency.

From this experiment, it was demonstrated that the modified Cre recombinase gene for mammals shows an extremely higher recombination frequency than the conventional one.

The modified Cre recombinase gene for mammals of the present invention has a notable advantage in that its expression level in bodies, organs, tissues or cells of mammals is several times as high as that of the wild-type virus-derived Cre recombinase gene. Since the expression level of the modified Cre recombinase is high in mammals, the site-specific recombination occurs in mammals with a significantly high frequency.

If the modified Cre recombinase gene for mammals of the present invention is used, it is possible to knock-in or knock-out a desired gene in a location-controlled and/or time-controlled manner with improved frequency.

If the method of the present invention is used, it is possible to create transgenic animals, organs, tissues or cells into or from which a specific gene is knocked-in or knocked-out in a location-controlled and/or time-controlled manner. The present invention has an immeasurable effect upon clinical medicine and the basic medical science including organ transplantation, gene therapy, and designed animal model for disorder.

Additional advantages and modifications will readily occur to those skilled in the art. Therefore, the invention in its broader aspects is not limited to the specific details and representative experiment shown and described herein. Accordingly, various modifications may be made without departing from the spirit or scope of the general inventive concept as defined by the appended claims and their equivalents.

What is claimed is:

1. A polynucleotide comprising a modified Cre recombinase gene comprising SEQ ID NO:1; and an inducible promoter operatively linked to the modified Cre recombinase gene.

2. The polynucleotide according to claim 1, further comprising at least one of a marker gene, a nucleic acid encoding a nuclear transport signal, and a Kozak sequence.

3. The polynucleotide according to claim 1, wherein the inducible promoter is a thymidine kinase promoter.

4. A polynucleotide complementary to the entire sequence of the polynucleotide according to claim 1.

5. A cell into which the polynucleotide according to claim 1 is introduced, wherein an active Cre recombinase is expressed in the cell.

* * * * *

SEQUENCE LISTING

```
<160> NUMBER OF SEQ ID NOS: 6

<210> SEQ ID NO 1
<211> LENGTH: 1050
<212> TYPE: DNA
<213> ORGANISM: Artificial Sequence
<220> FEATURE:
<221> NAME/KEY: CDS
<222> LOCATION: (1)..(1050)
<220> FEATURE:
<221> NAME/KEY: misc_feature
<222> LOCATION: ()..()
<223> OTHER INFORMATION: Description of Artificial Sequence: synthetic
      dna

<400> SEQUENCE: 1 atg ccc aag aag aag agg aag gtg agc aac ctg ctg acc gtg cac cag        48
Met Pro Lys Lys Lys Arg Lys Val Ser Asn Leu Leu Thr Val His Gln
1               5                   10                  15 aac ctg ccc gcc ctg ccc gtg gac gcc acc agc gac gag gtg cgc aag        96
Asn Leu Pro Ala Leu Pro Val Asp Ala Thr Ser Asp Glu Val Arg Lys
            20                  25                  30 aac ctg atg gac atg ttc cgc gac cgc cag gcc ttc agc gag cac acc       144
Asn Leu Met Asp Met Phe Arg Asp Arg Gln Ala Phe Ser Glu His Thr
        35                  40                  45 tgg aag atg ctg ctg agc gtg tgc cgc agc tgg gcc gcc tgg tgc aag       192
Trp Lys Met Leu Leu Ser Val Cys Arg Ser Trp Ala Ala Trp Cys Lys
    50                  55                  60 ctg aac aac cgc aag tgg ttc ccc gcc gag ccc gag gac gtg cgc gac       240
Leu Asn Asn Arg Lys Trp Phe Pro Ala Glu Pro Glu Asp Val Arg Asp
65                  70                  75                  80 tac ctg ctg tac ctg cag gcc cgc ggc ctg gcc gtg aag acc atc cag       288
Tyr Leu Leu Tyr Leu Gln Ala Arg Gly Leu Ala Val Lys Thr Ile Gln
                85                  90                  95 cag cac ctg ggc cag ctg aac atg ctg cac cgc cgc agc ggc ctg ccc       336
Gln His Leu Gly Gln Leu Asn Met Leu His Arg Arg Ser Gly Leu Pro
            100                 105                 110
```

```
cgc ccc agc gac agc aac gcc gtg agc ctg gtg atg cgc cgc atc cgc     384
Arg Pro Ser Asp Ser Asn Ala Val Ser Leu Val Met Arg Arg Ile Arg
        115                 120                 125 aag gag aac gtg gac gcc ggc gag cgc gcc aag cag gcc ctg gcc ttc     432
Lys Glu Asn Val Asp Ala Gly Glu Arg Ala Lys Gln Ala Leu Ala Phe
    130                 135                 140 gag cgc acc gac ttc gac cag gtg cgc agc ctg atg gag aac agc gac     480
Glu Arg Thr Asp Phe Asp Gln Val Arg Ser Leu Met Glu Asn Ser Asp
145                 150                 155                 160 cgc tgc cag gac atc cgc aac ctg gcc ttc ctg ggc atc gcc tac aac     528
Arg Cys Gln Asp Ile Arg Asn Leu Ala Phe Leu Gly Ile Ala Tyr Asn
                165                 170                 175 acc ctg ctg cgc atc gcc gag atc gcc cgc atc cgc gtg aag gac atc     576
Thr Leu Leu Arg Ile Ala Glu Ile Ala Arg Ile Arg Val Lys Asp Ile
            180                 185                 190 agc cgc acc gac ggc ggc cgc atg ctg atc cac atc ggc cgc acc aag     624
Ser Arg Thr Asp Gly Gly Arg Met Leu Ile His Ile Gly Arg Thr Lys
        195                 200                 205 acc ctg gtg agc acc gcc ggc gtg gag aag gcc ctg agc ctg ggc gtg     672
Thr Leu Val Ser Thr Ala Gly Val Glu Lys Ala Leu Ser Leu Gly Val
    210                 215                 220 acc aag ctg gtg gag cgc tgg atc agc gtg agc ggc gtg gcc gac gac     720
Thr Lys Leu Val Glu Arg Trp Ile Ser Val Ser Gly Val Ala Asp Asp
225                 230                 235                 240 ccc aac aac tac ctg ttc tgc cgc gtg cgc aag aac ggc gtg gcc gcc     768
Pro Asn Asn Tyr Leu Phe Cys Arg Val Arg Lys Asn Gly Val Ala Ala
                245                 250                 255 ccc agc gcc acc agc cag ctg agc acc cgg gcc ctg gag ggc atc ttc     816
Pro Ser Ala Thr Ser Gln Leu Ser Thr Arg Ala Leu Glu Gly Ile Phe
            260                 265                 270 gag gcc acc cac cgc ctg atc tac ggc gcc aag gac gac agc ggc cag     864
Glu Ala Thr His Arg Leu Ile Tyr Gly Ala Lys Asp Asp Ser Gly Gln
        275                 280                 285 cgc tac ctg gcc tgg agc ggc cac agc gcc cgc gtg ggc gcc gcc cgc     912
Arg Tyr Leu Ala Trp Ser Gly His Ser Ala Arg Val Gly Ala Ala Arg
    290                 295                 300 gac atg gcc cgc gcc ggc gtg agc atc ccc gag atc atg cag gcc ggc     960
Asp Met Ala Arg Ala Gly Val Ser Ile Pro Glu Ile Met Gln Ala Gly
305                 310                 315                 320 ggc tgg acc aac gtg aac atc gtg atg aac tac atc cgc aac ctg gac    1008
Gly Trp Thr Asn Val Asn Ile Val Met Asn Tyr Ile Arg Asn Leu Asp
                325                 330                 335 agc gag acc ggc gcc atg gtg cgc ctg ctg gag gac ggc gac              1050
Ser Glu Thr Gly Ala Met Val Arg Leu Leu Glu Asp Gly Asp
        340                 345                 350

<210> SEQ ID NO 2
<211> LENGTH: 350
<212> TYPE: PRT
<213> ORGANISM: Artificial Sequence
<220> FEATURE:
<221> NAME/KEY: misc_feature
<222> LOCATION: ()..()
<223> OTHER INFORMATION: Description of Artificial Sequence: synthetic
      peptide

<400> SEQUENCE: 2

Met Pro Lys Lys Arg Lys Val Ser Asn Leu Leu Thr Val His Gln
1               5                   10                  15

Asn Leu Pro Ala Leu Pro Val Asp Ala Thr Ser Asp Glu Val Arg Lys
            20                  25                  30
```

```
Asn Leu Met Asp Met Phe Arg Asp Arg Gln Ala Phe Ser Glu His Thr
         35                  40                  45

Trp Lys Met Leu Leu Ser Val Cys Arg Ser Trp Ala Ala Trp Cys Lys
     50                  55                  60

Leu Asn Arg Lys Trp Phe Pro Ala Glu Pro Glu Asp Val Arg Asp
 65                  70                  75                  80

Tyr Leu Leu Tyr Leu Gln Ala Arg Gly Leu Ala Val Lys Thr Ile Gln
                 85                  90                  95

Gln His Leu Gly Gln Leu Asn Met Leu His Arg Arg Ser Gly Leu Pro
             100                 105                 110

Arg Pro Ser Asp Ser Asn Ala Val Ser Leu Val Met Arg Arg Ile Arg
             115                 120                 125

Lys Glu Asn Val Asp Ala Gly Glu Arg Ala Lys Gln Ala Leu Ala Phe
         130                 135                 140

Glu Arg Thr Asp Phe Asp Gln Val Arg Ser Leu Met Glu Asn Ser Asp
145                 150                 155                 160

Arg Cys Gln Asp Ile Arg Asn Leu Ala Phe Leu Gly Ile Ala Tyr Asn
                 165                 170                 175

Thr Leu Leu Arg Ile Ala Glu Ile Ala Arg Ile Arg Val Lys Asp Ile
                 180                 185                 190

Ser Arg Thr Asp Gly Gly Arg Met Leu Ile His Ile Gly Arg Thr Lys
         195                 200                 205

Thr Leu Val Ser Thr Ala Gly Val Glu Lys Ala Leu Ser Leu Gly Val
     210                 215                 220

Thr Lys Leu Val Glu Arg Trp Ile Ser Val Ser Gly Val Ala Asp Asp
225                 230                 235                 240

Pro Asn Asn Tyr Leu Phe Cys Arg Val Arg Lys Asn Gly Val Ala Ala
                 245                 250                 255

Pro Ser Ala Thr Ser Gln Leu Ser Thr Arg Ala Leu Glu Gly Ile Phe
             260                 265                 270

Glu Ala Thr His Arg Leu Ile Tyr Gly Ala Lys Asp Asp Ser Gly Gln
         275                 280                 285

Arg Tyr Leu Ala Trp Ser Gly His Ser Ala Arg Val Gly Ala Ala Arg
     290                 295                 300

Asp Met Ala Arg Ala Gly Val Ser Ile Pro Glu Ile Met Gln Ala Gly
305                 310                 315                 320

Gly Trp Thr Asn Val Asn Ile Val Met Asn Tyr Ile Arg Asn Leu Asp
                 325                 330                 335

Ser Glu Thr Gly Ala Met Val Arg Leu Leu Glu Asp Gly Asp
             340                 345                 350

<210> SEQ ID NO 3
<211> LENGTH: 34
<212> TYPE: DNA
<213> ORGANISM: Artificial Sequence
<220> FEATURE:
<221> NAME/KEY: misc_feature
<222> LOCATION: ()..()
<223> OTHER INFORMATION: Description of Artificial Sequence: synthetic
      DNA

<400> SEQUENCE: 3
ataacttcgt atagcataca ttatacgaag ttat                           34

<210> SEQ ID NO 4
<211> LENGTH: 29
```

```
<212> TYPE: DNA
<213> ORGANISM: Artificial Sequence
<220> FEATURE:
<221> NAME/KEY: misc_feature
<222> LOCATION: ()..()
<223> OTHER INFORMATION: Description of Artificial Sequence: synthetic
      DNA

<400> SEQUENCE: 4
ttcgtatagc atagattata cgaagttat                                    29

<210> SEQ ID NO 5
<211> LENGTH: 29
<212> TYPE: DNA
<213> ORGANISM: Artificial Sequence
<220> FEATURE:
<221> NAME/KEY: misc_feature
<222> LOCATION: ()..()
<223> OTHER INFORMATION: Description of Artificial Sequence: synthetic
      DNA

<400> SEQUENCE: 5
ataacttcgt atagcataca ttatacgaa                                    29

<210> SEQ ID NO 6
<211> LENGTH: 21
<212> TYPE: DNA
<213> ORGANISM: Artificial Sequence
<220> FEATURE:
<221> NAME/KEY: misc_feature
<222> LOCATION: ()..()
<223> OTHER INFORMATION: Description of Artificial Sequence: synthetic
      DNA

<400> SEQUENCE: 6
cccaagaaga agaggaaggt g                                            21
```